US010463246B2

(12) United States Patent
Garoon et al.

(10) Patent No.: US 10,463,246 B2
(45) Date of Patent: Nov. 5, 2019

(54) PERSONAL MONITORING FOR VISION LOSS FROM MACULAR DEGENERATION

(71) Applicant: Amslerapp, Des Plaines, IL (US)

(72) Inventors: Ira Garoon, Des Plaines, IL (US); Robert Garoon, Northbrook, IL (US)

(73) Assignee: AMSLERAPP, Des Plaines, IL (US)

( * ) Notice: Subject to any disclaimer, the term of this patent is extended or adjusted under 35 U.S.C. 154(b) by 0 days.

(21) Appl. No.: 15/205,755

(22) Filed: Jul. 8, 2016

(65) Prior Publication Data
US 2018/0008142 A1    Jan. 11, 2018

(51) Int. Cl.
*A61B 3/02* (2006.01)
*A61B 3/10* (2006.01)
*A61B 3/14* (2006.01)
*A61B 3/00* (2006.01)
*A61B 3/032* (2006.01)

(52) U.S. Cl.
CPC ............ *A61B 3/032* (2013.01); *A61B 3/0025* (2013.01); *A61B 3/0033* (2013.01)

(58) Field of Classification Search
CPC ........... A61B 3/032; A61B 3/024; A61B 3/08; A61B 3/103; A61B 3/14; A61B 3/113; A61B 3/1225; A61B 3/02; A61B 3/18; A61B 3/1015
USPC ............... 351/223, 222, 200, 201, 205, 206, 351/209–210, 221, 239, 243–246
See application file for complete search history.

(56) References Cited

U.S. PATENT DOCUMENTS

| | | |
|---|---|---|
| 5,892,570 A | 4/1999 | Stevens |
| 8,047,652 B1 | 11/2011 | Collazo |
| 2006/0111620 A1* | 5/2006 | Squilla ............... A61B 5/00 600/300 |
| 2007/0200927 A1* | 8/2007 | Krenik ............... A61B 3/032 348/47 |
| 2007/0268455 A1* | 11/2007 | Roser ............... A61B 3/032 351/223 |
| 2014/0285769 A1* | 9/2014 | Palanker ............ G06Q 50/22 351/223 |
| 2016/0262608 A1* | 9/2016 | Krueger ............ A61B 3/0041 |

FOREIGN PATENT DOCUMENTS

WO    2014022850 A1    2/2014

* cited by examiner

*Primary Examiner* — Dawayne Pinkney
(74) *Attorney, Agent, or Firm* — Amin, Turocy & Watson, LLP (57) ABSTRACT

Described is a system that provides a vision test that may be implemented on various types of devices including a personal device such as a smartphone. The system may track potential vision abnormalities across an extended period of time by utilizing a comparison algorithm to compare results of vision tests to automatically determine whether the vision abnormality such as macular degeneration has progressed for a patient. Accordingly, the system provides an effective tool that may be deployed across a large portion of the population to provide early detection of potential vision loss.

20 Claims, 10 Drawing Sheets

PERSONAL MONITORING FOR VISION LOSS FROM MACULAR DEGENERATION

TECHNICAL FIELD

This disclosure generally relates to the field of vision loss testing. More specifically, this disclosure relates to a system for monitoring a progression of potential vision loss from macular degeneration.

BACKGROUND

Macular degeneration is a prevalent cause of visual loss among older adults and is typically characterized by the development of pigmentary changes, neovascularization, hemorrhages, and edema in the macula. These changes gradually destroy the sensitivity of portions of the macula and may potentially lead to metamorphopsia, which is a geometric distortion of the visual field. However, if these pathological changes are detected early, procedures may delay or even prevent the development of advanced disease. Thus, early detection of macular degeneration is a critical tool in the treatment of this potentially severe condition. Obtaining an early diagnosis, however, typically requires a patient to visit an eye care professional on a regular basis, which is not always feasible for large portions of the population. Accordingly, self-administered vision testing tools have been developed to attempt to address issues with accessibility of eye care services. These self-administered testing tools, however, often rely on the patient to appropriately administer the tests and often still require coordination with an eye care professional. For example, a patient may perform a self-administered test, but is then required to electronically transmit the results to an eye care professional for diagnosis. In addition, these self-administered tests are not always suitable for determining changes in vision as they often require a patient to remember previous test results. Accordingly, current self-diagnostic vision testing tools are often not suitable for determining whether a patient is suffering from an increase in vision loss.

SUMMARY

In one embodiment, described is a method of monitoring for a progression of a vision abnormality. The method may include displaying a testing image suitable for detecting a vision abnormality for a user and receiving an input identifying a first irregularity perceived by a user within the testing image. The method may also include retrieving a second irregularity within the testing image previously identified by the user and determining a result for the vision abnormality for the user by comparing the first irregularity with the second irregularity.

In another embodiment, described is a device for monitoring for a progression of macular degeneration of a user. The device may include a processor configured to display an amsler grid for detecting a macular degeneration for a user and receive a touch input on the display identifying an area of a distortion perceived by the user within the amsler grid. The processor may also retrieve a previous distortion within the amsler grid previously identified by the user and determine whether the macular degeneration of the user has progressed by comparing the distortion with the previous distortion.

In yet another embodiment, described is a method of monitoring for a progression of a vision abnormality based on an initial and subsequent vision test. The method may include displaying a first testing image suitable for detecting a vision abnormality for a user as part of an initial vision test and receiving a first input identifying a first irregularity perceived by the user within the first testing image. The method may include storing the first irregularity perceived by the user and displaying a second testing image as part of a subsequent vision test. The method may include receiving a second input identifying a second irregularity perceived by the user within the second testing image and determining a progression of the vision abnormality for the user by comparing the first identified irregularity with the second identified irregularity.

DETAILED DESCRIPTION

Various embodiments and aspects will be described with reference to details discussed below, and the accompanying drawings will illustrate the various embodiments. The following description and drawings are illustrative and are not to be construed as limiting. Numerous specific details are described to provide a thorough understanding of various embodiments. However, in certain instances, well-known or conventional details are not described in order to provide a concise discussion of embodiments. In addition, reference in the specification to "one embodiment" or "an embodiment" means that a particular feature, structure, or characteristic described in conjunction with the embodiment can be included in at least one embodiment. The appearances of the phrase "in one embodiment" in various places in the specification do not necessarily all refer to the same embodiment.

In one embodiment, described is a system for personal monitoring for a progression of a loss of vision from macular degeneration. As described, early detection of macular degeneration is a critical tool for treating such a disease. A common clinical approach for detecting macular degeneration is to utilize an amsler grid for a vision test. An amsler grid is typically a printed square grid (e.g. 10 cm wide and 10 cm high), containing equally spaced parallel horizontal and vertical lines. Typical variations of the grid include individual squares of equal area (e.g. 5 mm×5 mm) arranged around a fixation point (e.g. a dot) at the center of the grid.

In use, the grid is held at approximately arm's length (e.g. a distance of about 30 cm) with a visual angle approximately 1 degree or less. While one eye is occluded, a patient (e.g. user) fixates on the central fixation point and then describes how the remainder of the grid appears. The patient may be asked a series of questions in order to determine if the patient perceives irregularities within the grid. These irregularities may include, for example, missing or faint areas, distortions within the image including a distortion of lines (e.g. lines that are wavy, crooked, blurry, etc.), differences in color, or any other type of irregularities. Typically, the patient is asked to identify and record these irregularities, for example, by drawing an outline around such areas. The patient is also asked to report any changes in the severity or distribution of the irregularities, which is an indicator of a progression of the degeneration. One problem with such a technique, however, is that the detection of the progression of the degeneration is often unrecognized because of the inability to accurately recall earlier identified irregularity patterns. Accordingly, it is often difficult to evaluate modest changes between test results.

In one embodiment, described is a system that provides a vision test that may be implemented (e.g. via an "app" or program) on a personal device (e.g. a smartphone). In one embodiment, the system may track potential vision abnormalities across an extended period of time by utilizing a comparison algorithm to compare results of vision tests to automatically determine whether the vision abnormality such as macular degeneration has progressed for a patient. Accordingly, in one embodiment, the system may be easily deployed to a large portion of the population to provide an effective tool for early detection of a progression of a potential loss of vision.

Figure 1:
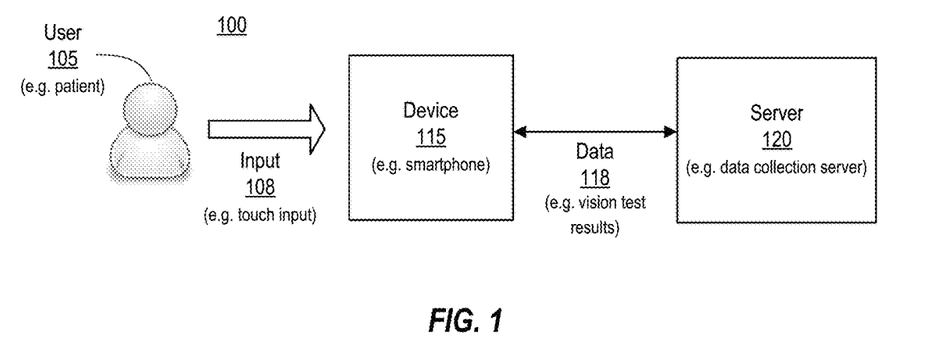
FIG. 1 is a block diagram illustrating an example operating environment for a vision testing system according to an embodiment of the disclosure.

In one embodiment, the system may be deployed within an operating environment. FIG. 1 is a block diagram illustrating an example operating environment for a vision testing system according to an embodiment of the disclosure. As shown, the operating environment 100 may include a device 115 and a server 120. A user 105 (or patient, or subject) may provide an input 108 to the device 115 as part of a vision test as further described herein. The device 115 may be any type of device including a smartphone, tablet, laptop, desktop, VR headset, set-top-box, and the like. The input 108 may include any suitable type of input that provides an indication of irregularities that may be perceived within a testing image. For example, in one embodiment, the input 108 may be in the form of a touch input to a touch sensitive display screen coupled to the device 115. The device 115 may communicate with a server 120 by transmitting data 118 via a network. For example, in one embodiment, the device 115 may retrieve data related to previous test results of the user 105 which may be stored centrally on the server 120 (e.g. data collection server), along with additional information associated with the user 105 such as characteristic information including demographic information or medical history information of the user. As further described herein, the stored data 118 may be used to aid in providing a preliminary diagnostic result of a potential vision abnormality for the user 105.

In addition to providing an input to a touch display of a smartphone, other configurations are also contemplated. For example, in another embodiment, the device 115 may be part of a larger system such as a kiosk that may be deployed, for example, at a health services facility. For instance, the kiosk may include a larger display screen that may provide increased accuracy or precision for vision testing. In another embodiment, the device 115 may be part of a system that utilizes a VR (e.g. virtual reality) type headset in conjunction with one or more tracking cameras to recognize touchless in-air input gestures. For instance, a user may wear a VR type headset that displays the testing image, and the tracking cameras may recognize an in-air gesture input indicating an area in which the user perceives a vision irregularity. Accordingly, the system may reconcile the in-air gesture with a portion of the displayed testing image to replicate the effect of a user physically outlining the distortion, for example, on a physical paper-based chart. One benefit of a VR type headset is that the user's full field of vision may be tested rather than a being limited to a physical paper-based chart/display traditionally used. Other suitable configurations are also contemplated. It should be noted that the network described in the operating environment 100 may be any suitable type of wired or wireless network such as a local area network (LAN), a wide area network (WAN), or combination thereof, and the server 120 may be any kind of server or a cluster of servers (e.g. cloud-based server)

Figure 2:
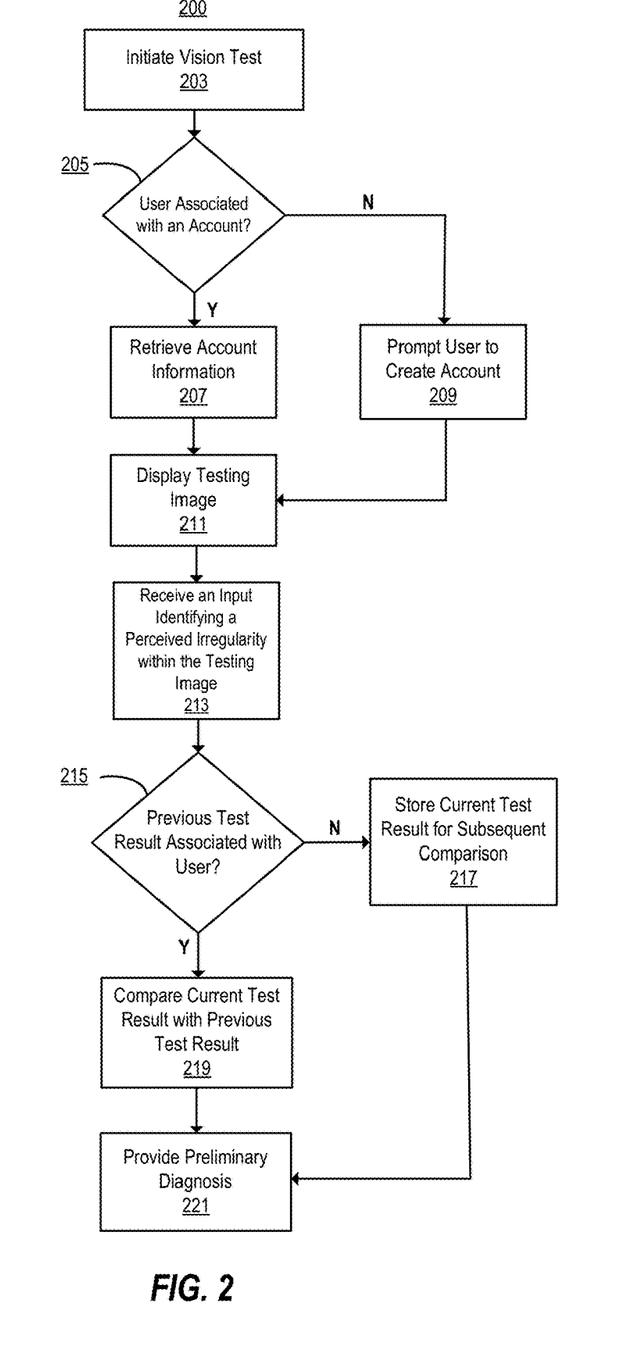
FIG. 2 is a flowchart of an example process of testing for a vision abnormality according to an embodiment of the disclosure.
Figure 3:
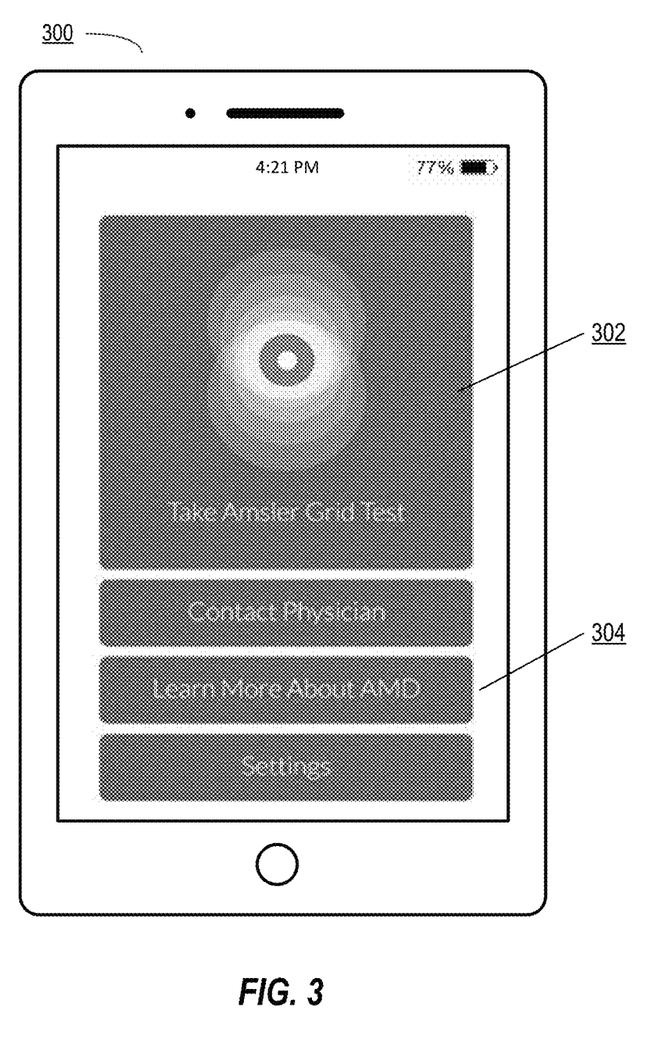
FIG. 3 is an example diagram of an interface for a vision testing system according to an embodiment of the disclosure.

FIG. 2 is a flowchart of an example process of testing for a vision abnormality according to an embodiment of the disclosure. The process 200 may be performed by components within system 100 (e.g. device 115 or server 120). In process 200, the system may initiate a vision test 203. In one embodiment, the vision test may be part of an application installed on the device (e.g. device 115). FIG. 3 is an example diagram of an interface for a vision testing system according to an embodiment of the disclosure. As shown, the application may be implemented on a smartphone or tablet type device 300. In this example, the interface may include an option to launch the application 302 (e.g. "Take Amsler Grid Test"). In addition, other options 304 may also be provided. For example, as shown, options to obtain physician contact information may be provided as well as an option to learn more about age-related macular degeneration (ARMD). In addition, an option to specify settings for the application may be provided. These setting may include various settings or user preferences such as notifications or privacy settings. For example, the setting may include specifying when and how a user receives a reminder for taking subsequent vision tests.

Returning to FIG. 2, information may be associated with particular users, and accordingly, in operation 205, the system may determine whether a user (e.g. user 105) is associated with an account. If so, the system may prompt the user to provide login information and retrieve account information associated with the user in operation 207. If the user is not associated with an account, the system in operation 209 may prompt the user to create a new account. The account may be used to associate previous vision test results with the user. In addition, characteristic information may also be associated with a user account. For example, age, sex, location, ethnicity, medical records or other health related information may be associated with the user. In one embodiment, the system may even retrieve medical records associated with the user from a third-party provider (e.g.

hospital or insurance provider). As described further herein, the information described above may be associated with a vision test result and stored in a data collection server to aid in providing diagnosis information (or research information).

In order to conduct the vision test, the system may display a testing image in operation 211. The image may be any image for testing vision, and in one embodiment, the testing image may be an amsler grid as described above. In one embodiment, the testing image may be specific to a particular user. For example, if it is determined that a particular user may be prone to a particular vision abnormality, the system may provide a specific testing image for the abnormality. In another example, a specific testing image may be provided based on previous test results for the user. In addition, the testing image may also be dynamically adapted based on the particular user, or test results for the user. For example, after receiving the input from a user identifying an irregularity within the testing image (e.g. distortion), the system may provide a subsequent variant of the testing image that is adapted based on the input to confirm the irregularity or to further isolate the location of the perceived irregularity. For example, the number, size, color, and spacing of grid lines may be adapted based on test results for the user.

As referred to herein, a vision abnormality may be any abnormality, for example, diagnosable based on a vision test. For example, in one embodiment, the vision abnormality may relate to vision loss from macular degeneration (or ARMD) including metamorphopsia and various variants or sub-types of such conditions.

Figure 4:
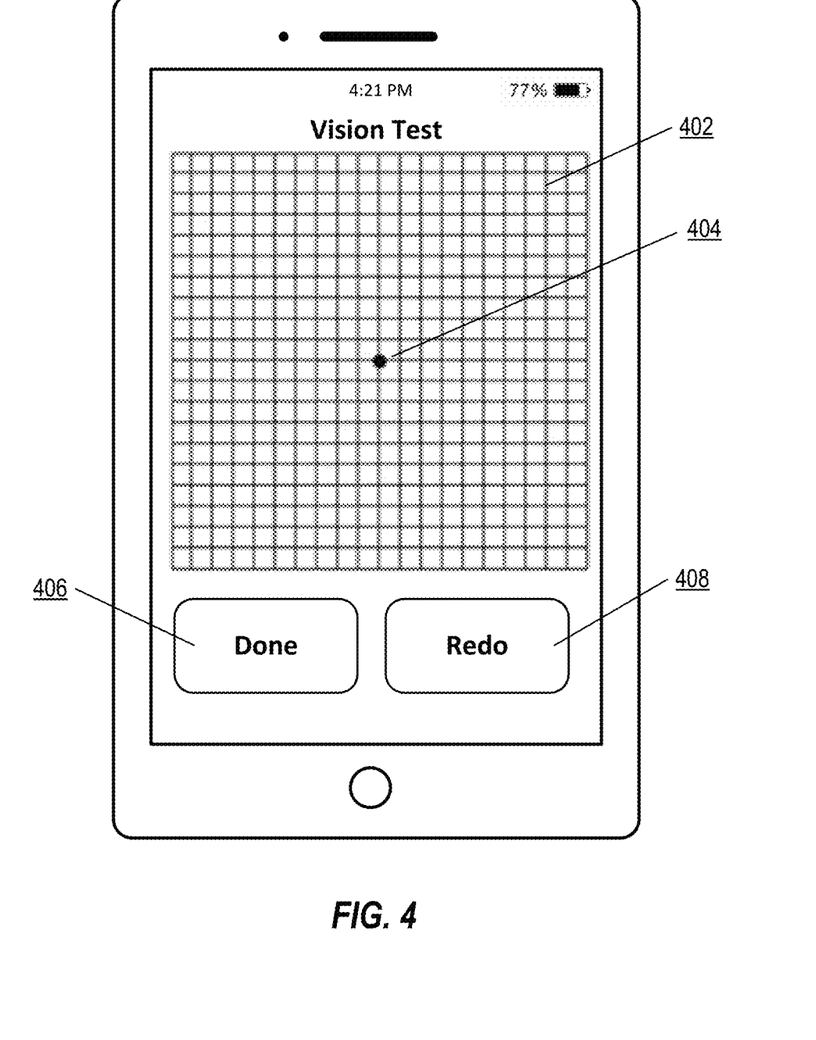
FIG. 4 is an example diagram of an amsler grid for the vision testing system according to an embodiment of the disclosure.

Next, as part of the vision test, the system in operation 213 may receive an input from the user identifying a first irregularity perceived within the testing image. The input may include a selection of one or more portions of the testing image. For example, the perceived irregularity may include a selection of a single location or area of the testing image, or multiple locations or areas within the testing image. As described, in one embodiment, the input may identify a distortion within an amsler grid. FIG. 4 is an example diagram of an amsler grid for the vision testing system according to an embodiment of the disclosure. As shown, the amsler grid may include a grid 402 portion that includes a fixation point 404 at the center of the grid 402. The interface may also include one or more elements such as buttons that may be used to submit 406 (e.g. "Done") or redo 408 (e.g. "Redo") a selection of an area of the grid corresponding to a perceived irregularity. In addition, in one embodiment, the system may provide instructions to the user (e.g. via the display interface or other means such as audio instructions) for identifying any irregularities perceived within the grid. For example, the instructions may include requesting the user to cover one eye and position the screen at a certain distance and at a certain angle. In addition, in some embodiments, the user may provide additional input further characterizing the irregularity perceived including the type of irregularity. For example, the user may be provided with additional options that may be selected such as whether the irregularity corresponds to missing or faint portions, distortions with the image such as wavy lines, etc., or other types of irregularities.

Figure 5:
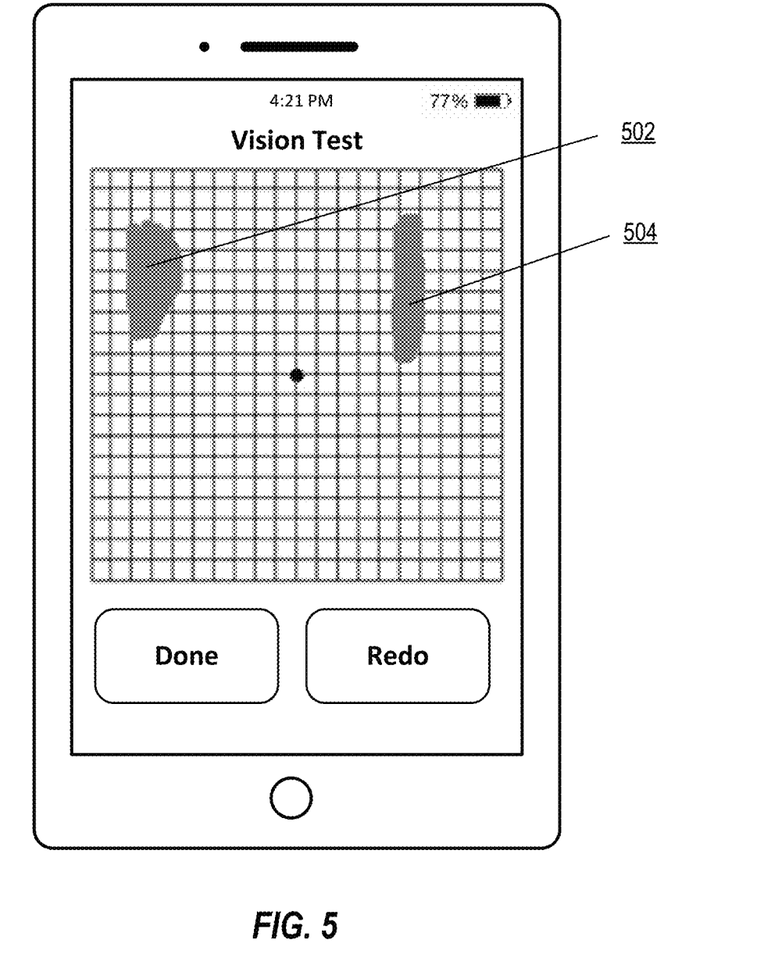
FIG. 5 is an example diagram showing identified portions corresponding to irregularities perceived by a user within an amsler grid according to an embodiment of the disclosure.

In one embodiment, sensors or cameras included within the device may aid in determining whether the device (e.g. screen) is positioned correctly. For example, gyroscopes may determine whether the device is positioned at a correct angle and a camera (e.g. front-facing camera) may determine whether the device is at a correct distance from the user. For example, the camera may determine distance information based on a captured size of one or more objects (e.g. a user's face). Accordingly, a user may then provide an input (e.g. touch input) to the screen to identify any irregularities perceived within the image. FIG. 5 is an example diagram showing identified portions corresponding to irregularities perceived by a user within an amsler grid according to an embodiment of the disclosure. As shown in this example, the user has indicated that a first portion 502 and a second portion 504 of the amsler grid correspond to a perceived irregularity within the grid (e.g. distorted lines within the grid). Accordingly, this information may be used as part of a preliminary diagnosis as further described herein.

Figure 6A:
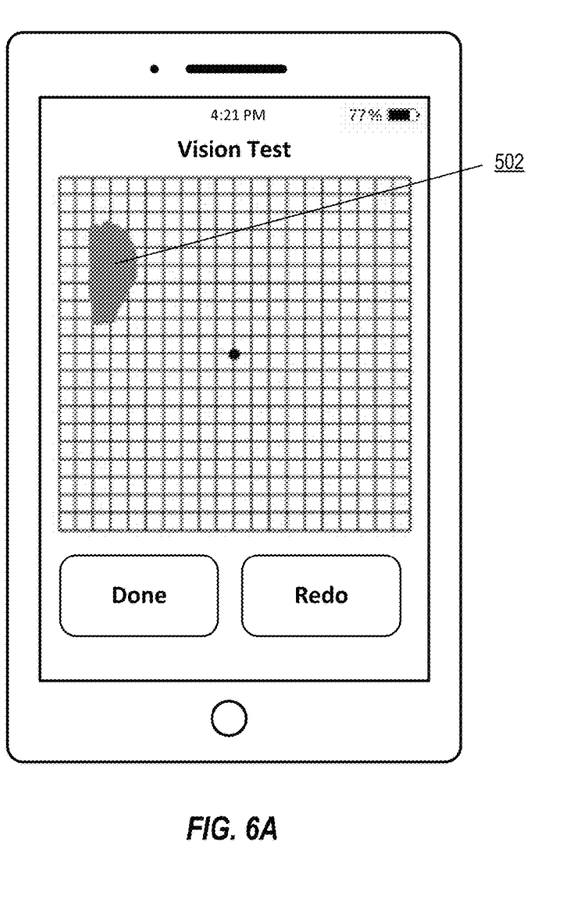
FIG. 6A is an example diagram showing a previous test result for the vision testing system according to an embodiment of the disclosure.
Figure 6B:
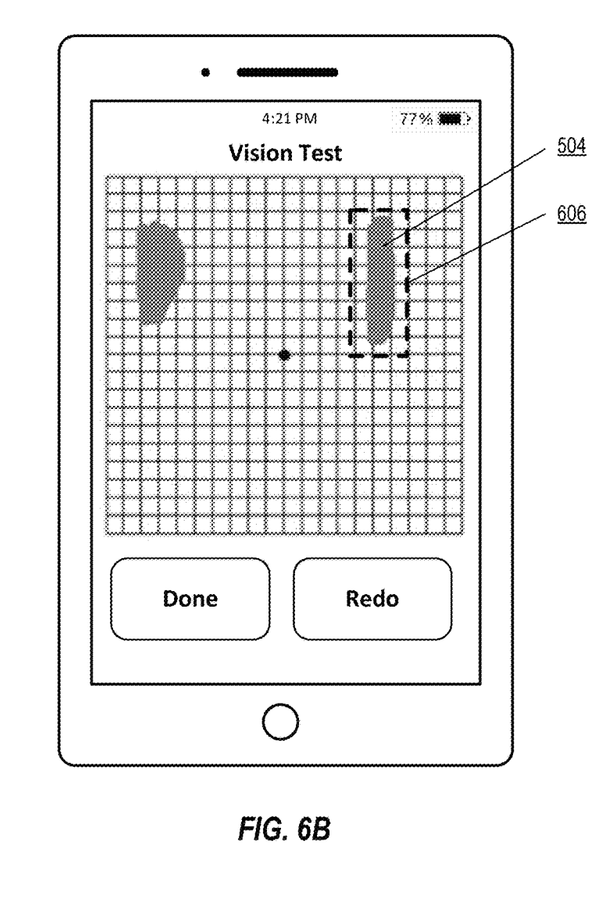
FIG. 6B is an example diagram showing a current test result of a vision testing system according to an embodiment of the disclosure.
Figure 7:
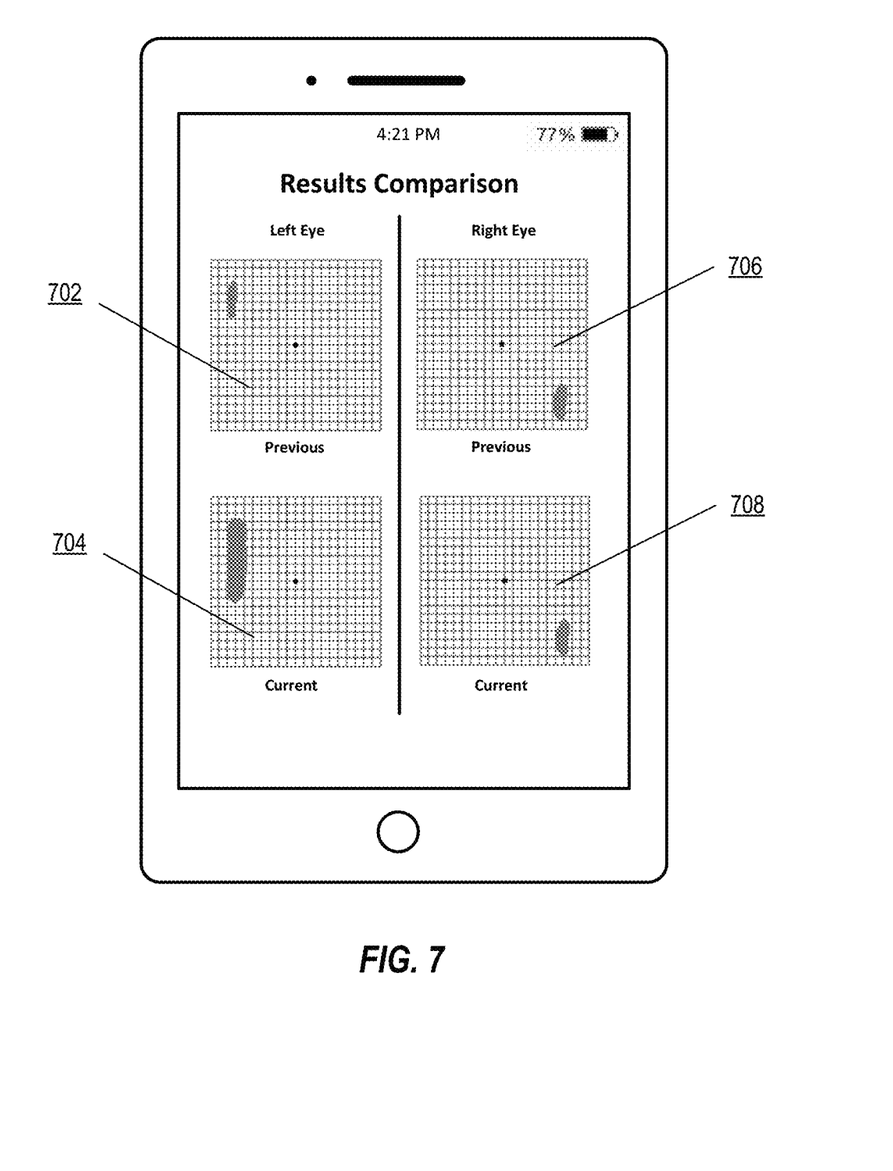
FIG. 7 is an example diagram showing a previous test result displayed concurrently with a current test result according to an embodiment of the disclosure.

Returning to FIG. 2, once a user has provided input with respect to any perceived irregularities, the system may determine whether there are any previous test results associated with the user in operation 215. If the user is not associated with any previous test results, the system may store the current test result for a subsequent comparison in operation 217. If the user is associated with one or more previous test results, the system may retrieve such results and compare the current test result with the retrieved previous test results in operation 219. The system may utilize a comparison algorithm to determine whether there is a progression of a particular vision abnormality. The comparison may be performed on the device or at a server. The comparison algorithm may utilize various calculations based on various mathematical formulas including total area, sum, average, weighted sums, distance from fixation point, etc. For example, the system may determine the area of any perceived distortions are larger than the area of a previously perceived distortion. Accordingly, this would indicate that a vision abnormality such as macular degeneration has progressed. In another example, the system may consider the location of the perceived irregularity. For instance, the irregularity may be closer towards the central portion of the field of vision of the user, which may indicate a further loss of a field of vision. In yet another example, the system may consider the type of irregularity. For instance, certain irregularities such as blank or missing areas may be more severe than slight distortions of lines within the grid. FIG. 6A and FIG. 6B show an example of a comparison between a current test result and a previous test result. FIG. 6A is an example diagram showing a previous test result for the vision testing system according to an embodiment of the disclosure. FIG. 6B is an example diagram showing a current test result of a vision testing system according to an embodiment of the disclosure. As shown in these figures, the irregularity corresponding to portion 502 remains and portion 504 is a newly discovered irregularity. Accordingly, the system, as shown in 606, may identify and indicate to the user that one of the portions identified in the current test is a newly perceived irregularity. In one embodiment, the system may display both the previous test results along with current test results. FIG. 7 is an example diagram showing a previous test result displayed concurrently with a current test result according to an embodiment of the disclosure. In one embodiment, the system may display previous test results and current test results at the same time. As shown in this example, the system may display previous test results (702 and 706) along with current test results (704 and 708) for each eye. As shown, based on the results, the system (and user) may determine the identified irregularity for the right eye has remained the same. As shown, based on the results for the left eye, however, the system may inform the user that the area of an identified irregularity in the current test result for the left eye 704 is larger than the area of an identified irregularity in the previous test result for the left eye the left 702. Accordingly, the system (and user) may determine that the vision abnormality (e.g. macular degeneration) in the left eye has progressed. Accordingly, the system has provided a preliminary diagnosis that the loss of vision has potentially progressed in the user's left eye.

Returning the FIG. 2, as shown in the examples discussed in FIGS. 6A-B and 7, the system may provide a preliminary diagnosis in operation 221. For example, in one embodiment, the system may indicate that there has been a progression of macular degeneration. Accordingly, in some embodiments, the system not only receives input from the user, but also performs an automatic comparison to provide an immediate result to the user. In such a situation, the user may now be aware that a potential loss of vision has progressed, and thus, may be notified that further action such as visiting an eye care professional (e.g. optometrist, ophthalmologist, retina specialist, etc.) is warranted. It should be noted that the system provides a preliminary diagnosis and does not necessarily substitute diagnosis by an actual eye care professional. The system does, however, in some circumstances alert a user that a vision abnormality may have progressed. Accordingly, the system described herein provides an effective tool for earlier detection and prevention of disease related to potential loss of vision.

It should be noted that in addition to the interface screens described above (e.g. FIGS. 3-7), the system may display additional screens, options, or menu items. For example, the system may display information related to a preliminary diagnostic result provided by the system. This information may include various types of information including severity, type, prognosis, or other information related to the potential vision abnormality diagnosed for the user. In addition, the information may be determined based on analyzing data from a data collection server or database. For example, the system may retrieve test results of other users with similar test results or characteristics as the user. In addition, the system may even retrieve diagnosis or prognosis information that has been determined as a follow-up from an eye care professional. For example, the system may retrieve vision results of other users and provide statistical information relating to a diagnosis for the user. In another example, the statistical information may relate to statistics related to progression of the disease, treatments prescribed, surgery results, etc. Accordingly, by collecting vision test results, the system may provide statistical tools which may aid in an overall diagnostic capability of the system.

In one embodiment, the system may communicate with a personal monitoring device providing health information of the user. This information may be collected and provided along with the vision test results of the user. For example, the personal monitoring device may include a wearable device and the health information may include, for example, a heart rate, glucose level, and blood pressure of a user at the time or leading up to the vision test. Accordingly, this information may be used as part of the data collection and aid in providing statistical information related to diagnosed vision abnormalities.

Figure 8:
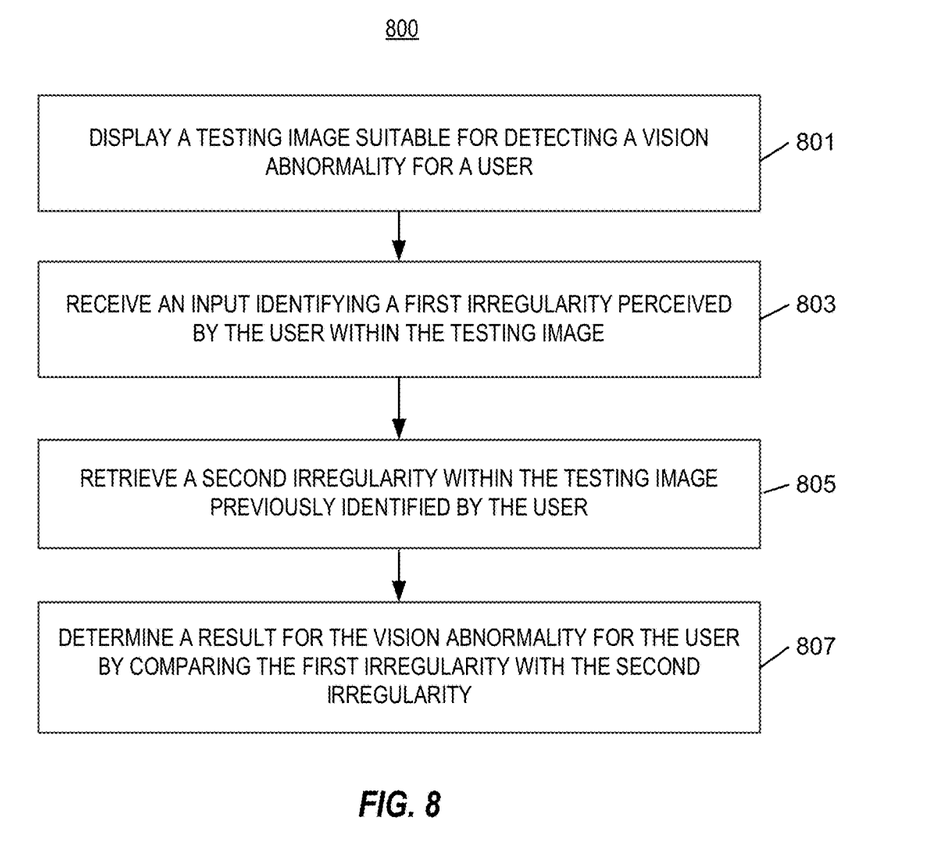
FIG. 8 is a flow diagram of determining a result for a vision abnormality by comparing irregularities perceived by a user within a testing image according to an embodiment of the disclosure.

FIG. 8 is a flow diagram of determining a result for a vision abnormality by comparing irregularities perceived by a user within a testing image according to an embodiment of the disclosure. Process 800 may use processing logic which may include software, hardware, or a combination thereof. For example, process 800 may be performed by a system (or device 115). In 801, the system may display, on a display, a testing image suitable for detecting a vision abnormality for a user. In 803, the system may receive, from the user, an input identifying a first irregularity perceived by the user within the testing image. In one embodiment, receiving the input identifying the first irregularity may include receiving a touch input to the display indicating an area of a distortion perceived by the user within the testing image. In 805, the system may retrieve a second irregularity within the testing image previously identified by the user. For example, the system may retrieve a previous test result associated with the user that may be stored locally (e.g. on the device) or centrally on a server (e.g. data collection server). In 807, the system may determine a result for the vision abnormality for the user by comparing the first irregularity with the second irregularity.

In one embodiment, the result of the vision abnormality may be determined automatically by the device and without human intervention. For example, other systems merely submit the test results to an eye care professional, which in turn then provide a diagnosis. In one embodiment, the system described herein may provide an immediate preliminary diagnosis to the user. For example, the preliminary diagnosis may indicate that the irregularity (e.g. area of distortion) is larger than in a previous test, and thus, the loss of vision may have increased or the degeneration may have progressed.

In one embodiment, comparing the first irregularity with the second irregularity may include determining the area of the distortion is larger than an area of a distortion within the testing image previously identified by the user. In addition, in one embodiment, determining the result of the vision abnormality may include comparing a first location of the first irregularity to a second location of the second irregularity and determining the first location relative to the second location corresponds to an increase in a loss of a field of vision of the user. For example, the system may determine that the irregularity is closer to a central portion of a user's field of vision which may be more severe than a loss of vision in a peripheral area of the user's field of vision. In another embodiment, determining the result of the vision abnormality may include determining the first irregularity corresponds to a first type of irregularity and the second irregularity corresponds to a second type of irregularity and determining the first type of irregularity relative to the second type of irregularity corresponds to a progression of macular degeneration. For example, the system may determine the type of distortion (e.g. missing or faint portions) correspond to a first type of irregularity which is more severe than a second type of irregularity (e.g. wavy lines). In addition, in one embodiment, in response to receiving the input identifying the first irregularity, the system may display a variant of the testing image and receive another input to confirm the first irregularity perceived by the user. For example, if the irregularity corresponds to missing lines, the system may display a grid with thicker lines or lines that are closer together. Accordingly, in some embodiments, the system may provide variants of the testing image to either confirm a perceived irregularity or to capture the irregularity with a higher degree of resolution or specificity.

Figure 9:
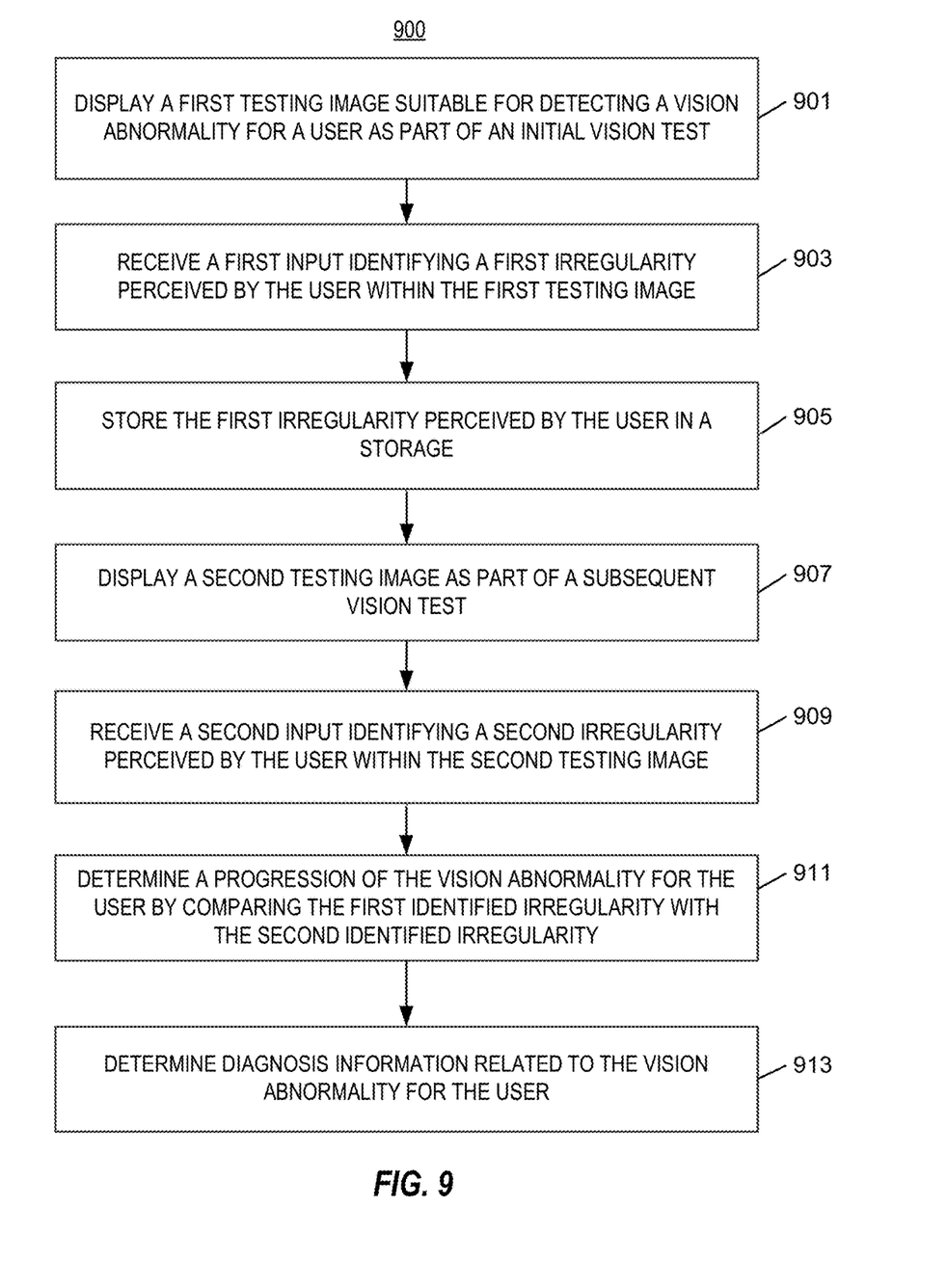
FIG. 9 is a flow diagram of determining a progression of a vision abnormality according to an embodiment of the disclosure.

FIG. 9 is a flow diagram of a method of determining a progression of a vision abnormality according to an embodiment of the disclosure. Process 900 may use processing logic which may include software, hardware, or a combination thereof. For example, process 900 may be performed by a system (or device 115). In 901, the system may display, on a display coupled to a device, a first testing image suitable for detecting a vision abnormality for a user as part of an initial vision test. In 903, the system may receive, from the user, a first input identifying a first irregularity perceived by the user within the first testing image. In 905, the system may store, in a storage, the first irregularity perceived by the user. In 907, the system may display, on the display, a second testing image as part of a subsequent vision test. In one embodiment, displaying the second testing image may include adapting the first testing image based on the first irregularity perceived by the user. In 909, the system may receive, from the user, a second input identifying a second irregularity perceived by the user within the second testing image. In 911, the system may determine a progression of the vision abnormality for the user by comparing the first identified irregularity with the second identified irregularity. In 913, the system may determine diagnosis information for the user related to the result of the vision abnormality. In one embodiment, the system may determine diagnosis information by determining a set of characteristics associated with the user, comparing the identified distortions perceived by the user with distortions perceived by other users with similar characteristics as the set of characteristics associated with the user, and retrieving information associated with diagnosed vision abnormalities of the other users. For example, the system may retrieve statistical information related to other users with similar test results. As described above, the statistical information may relate to diagnosis (e.g. ultimate diagnosis provided by an eye care professional), prognosis, surgical results, treatments, etc. In one embodiment, the information associated with diagnosed vision abnormalities of the other users may relate to information provided by a medical professional in response to analyzing the vision abnormalities of one or more of the other users. For example, the system may provide the preliminary diagnosis results to an eye care professional for confirmation or follow-up treatment. Additional information determined by the eye care professional may then be associated with the user and may be stored as part of a database to provide statistical information as described above.

It should be noted that there may be variations to the flow diagrams or the steps (or operations) described therein without departing from the embodiments described herein. For instance, the steps may be performed in parallel, simultaneously, a differing order, or steps may be added, deleted, or modified.

Figure 10:
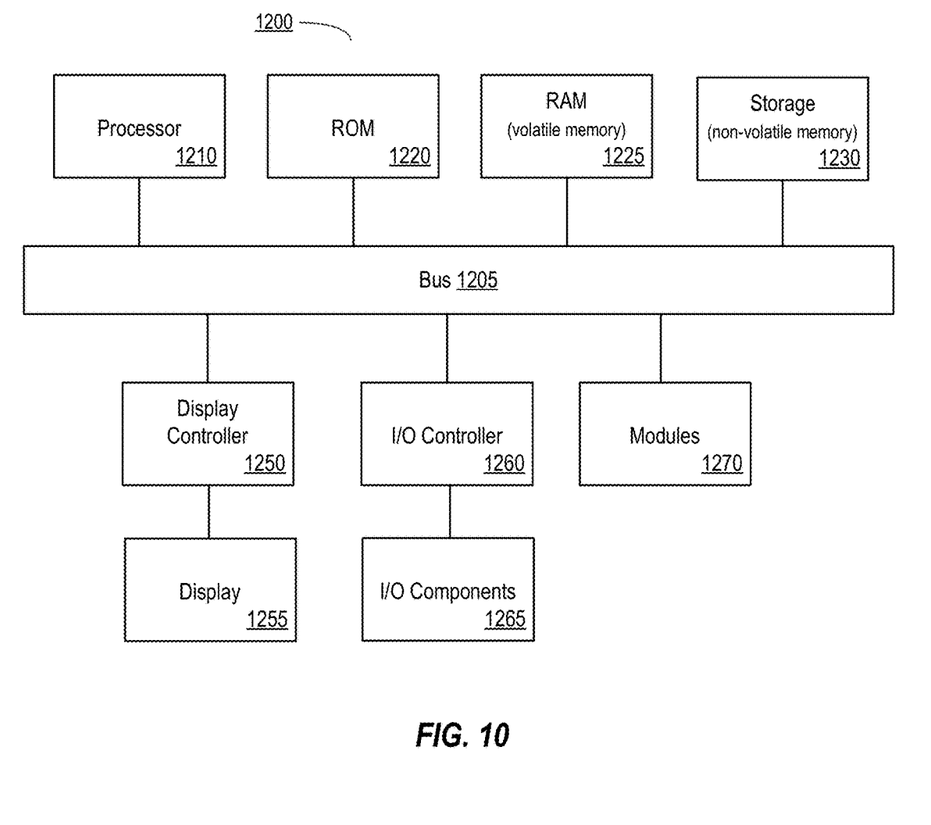
FIG. 10 is a block diagram illustrating an example computing system which may be used in conjunction with one or more of the embodiments of the disclosure.

FIG. 10 is a block diagram illustrating an example computing system which may be used in conjunction with one or more of the embodiments of the disclosure. For example, computing system 1200 (or system, or computing device, or device) may represent any of the systems, or devices described herein (e.g. device 115 or server 120) that perform any of the processes, operations, or methods of the disclosure. Note that while the computing system illustrates various components, it is not intended to represent any particular architecture or manner of interconnecting the components as such details are not germane to the present disclosure. It will also be appreciated that other types of systems that have fewer or more components than shown may also be used with the present disclosure.

As shown, the computing system 1200 may include a bus 1205 which may be coupled to a processor 1210, ROM (Read Only Memory) 1220, RAM (or volatile memory) 1225, and storage (or non-volatile memory) 1230. The processor 1210 may retrieve stored instructions from one or more of the memories 1220, 1225, and 1230 and execute the instructions to perform processes, operations, or methods described herein. These memories represent examples of a non-transitory machine-readable medium or storage containing instructions which when executed by a computing system (or a processor), cause the computing system (or processor) to perform operations, processes, or methods described herein. The RAM 1225 may be implemented as, for example, dynamic RAM (DRAM), or other types of memory that require power continually in order to refresh or maintain the data in the memory. Storage 1230 may include, for example, magnetic, semiconductor, tape, optical, removable, non-removable, and other types of storage that maintain data even after power is removed from the system. It should be appreciated that storage 1230 may be remote from the system (e.g. accessible via a network).

A display controller 1250 may be coupled to the bus 1205 in order to receive display data to be displayed on a display device 1255, which can display any one of the user interface features or embodiments described herein and may be a local or a remote display device. The computing system 1200 may also include one or more input/output (I/O) components 1265 including mice, keyboards, touch screen, network interfaces, printers, speakers, and other devices. Typically, the input/output components 1265 are coupled to the system through an input/output controller 1260.

Modules 1270 (or components, units, or logic) may represent any modules to implement any of the operations described above. Modules 1270 may reside, completely or at least partially, within the memories described above, or within a processor during execution thereof by the computing system. In addition, modules 1270 can be implemented as software, firmware, or functional circuitry within the computing system, or as combinations thereof.

It should be noted that the present disclosure recognizes that the use of personal information (e.g. vision test results), in the present technology, can be used to the benefit of users. The present disclosure further contemplates that the entities responsible for the collection, analysis, disclosure, transfer, storage, or other use of such personal information data will comply with well-established privacy policies and/or privacy practices. In particular, such entities may implement and consistently use privacy policies and practices that are generally recognized as meeting or exceeding industry or governmental requirements for maintaining personal information data private and secure. Further, in one embodiment, such collection may occur only after receiving the informed consent of the users. Additionally, such entities may take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

In the foregoing specification, example embodiments of the disclosure have been described. It will be evident that various modifications may be made thereto without departing from the broader spirit and scope of the disclosure as set forth in the following claims. The specification and drawings are, accordingly, to be regarded in an illustrative sense rather than a restrictive sense.

What is claimed is:

1. A non-transitory machine-readable medium storing instructions which, when executed by one or more processors of a device, cause the device to perform operations comprising:
employing, by the device being held by a user, at least one sensing device to determine a position of the device relative to the user, wherein the at least one sensing device comprises at least one gyroscope, and the position of the device relative to the user comprises an angle of a screen of the device relative to the eye of the user determined based on the at least one gyroscope;

in response to a determination that the position of the device relative to the user is not correct, presenting, by the device, instructions to the user to adjust the position of the device relative to the user to a defined position, wherein the defined position comprises a defined angle of the screen of the device relative to the eye of the user;

displaying, on a display coupled to the device, a testing image for detection of a vision abnormality for the user, wherein the testing image is displayed during a first test;

receiving, by the device, during the first test, an input identifying a first irregularity perceived by the user within the testing image;

retrieving, by the device, a second irregularity within the testing image, wherein the second irregularity was previously identified by the user during a second test that occurred prior to the first test; and determining, by the device, a result of the vision abnormality for the user by comparing the first irregularity with the second irregularity, wherein the comparing the first irregularity with the second irregularity comprises determining that a first area of a first distortion, associated with the first irregularity, is larger than a second area of a second distortion within the testing image previously identified by the user, and associated with the second irregularity.

2. The non-transitory machine-readable medium of claim 1, wherein the result of the vision abnormality is determined automatically by the device and without human intervention.

3. The non-transitory machine-readable medium of claim 1, wherein the testing image is an amsler grid, and wherein the receiving the input identifying the first irregularity comprises receiving a touch input to the display indicating the first area of the distortion perceived by the user within the testing image.

4. The non-transitory machine-readable medium of claim 1, wherein the determining the result of the vision abnormality comprises:
comparing a first location of the first irregularity to a second location of the second irregularity; and
determining that the first location relative to the second location corresponds to an increase in a loss of a field of vision of the user.

5. The non-transitory machine-readable medium of claim 1, wherein the determining the result of the vision abnormality comprises:
determining the first irregularity corresponds to a first type of irregularity and the second irregularity corresponds to a second type of irregularity different than the first type of irregularity; and
determining the first type of irregularity compared to the second type of irregularity corresponds to a progression of macular degeneration.

6. The non-transitory machine-readable medium of claim 1, further comprising based on receiving the input identifying the first irregularity, displaying a variant of the testing image and receiving another input to confirm the first irregularity perceived by the user.

7. A device, comprising:
a memory storing instructions; and
a processor coupled to the memory to execute the instructions from the memory, the processor configured to:
employ, by the device being held by a user, at least one sensing device to determine a position of the device relative to the user, wherein the at least one sensing device comprises at least one gyroscope, and the position of the device relative to the user comprises an angle of a screen of the device relative to the eye of the user determined based on the at least one gyroscope;

in response to a determination that the position of the device relative to the user is not correct, present, by the device, instructions to the user to adjust the position of the device relative to the user to a defined position, wherein the defined position comprises a defined angle of the screen of the device relative to the eye of the user;

display, on a display coupled to the device, an amsler grid to detect macular degeneration of the user;

receive, by the device, a touch input on the display identifying an area of a distortion perceived by the user within the amsler grid;

retrieve, by the device, a previous distortion within the amsler grid previously identified by the user;

determine the macular degeneration of the user has progressed by comparing the distortion with the previous distortion; and display, in response to receiving the input identifying the area of the distortion, a variant of the amsler grid, wherein the variant of the amsler grid comprises increasing or decreasing a number of grid lines within the amsler grid.

8. The device of claim 7, wherein the processor is further configured to receive another input to further isolate the area of the distortion perceived by the user in response to the display of the variant of the amsler grid.

9. The device of claim 7, wherein the processor is further configured to concurrently display the area of the distortion and the previous distortion perceived by the user.

10. The device of claim 7, wherein the processor is further configured to:
communicate with a personal monitoring device coupled to the device;
receive current health information of the user from the personal monitoring device; and
associate the current health information with the distortions perceived by the user.

11. The device of claim 10, wherein the personal monitoring device is a wearable device and the current health information comprises one or more of a heart rate, glucose level, or blood pressure.

12. The device of claim 7, wherein the at least one sensing device further comprises at least one camera.

13. A computer-implemented method of monitoring for potential vision abnormalities, comprising:
employing, by a device comprising a processor, at least one sensing device to determine a position of the device relative to a user, wherein the at least one sensing device comprises at least one gyroscope, and the position of the device relative to the user comprises an angle of a screen of the device relative to the eye of the user determined based on the at least one gyroscope, wherein the device is being held by the user;

in response to a determination that the position of the device relative to the user is not correct, presenting, by the device, instructions to the user to adjust the position of the device relative to the user to a defined position, wherein the defined position comprises a defined angle of the screen of the device relative to the eye of the user;

displaying, on a display coupled to a device, a first testing image suitable for detecting a vision abnormality for the user as part of an initial vision test;

receiving, at the device, a first input identifying a first irregularity perceived by the user within the first testing image;

storing, in a computer-readable storage medium of the device, the first irregularity perceived by the user;

displaying, on the display, a second testing image as part of a subsequent vision test, wherein the displaying the second testing image is performed after the displaying the first testing image and after the storing the first irregularity, wherein the displaying the second testing image comprises adapting the first testing image based on the first irregularity perceived by the user, the adapting comprising increasing or decreasing a thickness of grid lines within the amsler grid;

receiving, at the device and from the user, a second input identifying a second irregularity perceived by the user within the second testing image; and determining, by the device, a progression of the vision abnormality for the user by comparing the first identified irregularity received during the initial vision test with the second identified irregularity received during the subsequent vision test.

14. The computer-implemented method of claim 13, further comprising providing, by the device, a preliminary diagnosis based on the progression of the vision abnormality determined for the user.

15. The computer-implemented method of claim 13, wherein the first testing image is an amsler grid.

16. The computer-implemented method of claim 13, further comprising determining, by the device, diagnosis information for the user related to the vision abnormality, wherein the determining diagnosis information comprises:

determining a set of characteristics associated with the user;

comparing the irregularities perceived by the user with irregularities perceived by other users with similar characteristics as the set of characteristics associated with the user; and retrieving information associated with the preliminary diagnosis of the other users.

17. The computer-implemented method of claim 16, wherein the information associated with the preliminary diagnosis of the other users includes statistical information related to the vision abnormality.

18. The computer-implemented method of claim 16, wherein the information associated with the preliminary diagnosis of the other users relates to information provided by an eye care professional in response to analyzing the vision test results of the one or more of the other users.

19. The computer-implemented method of claim 13, wherein the at least one sensing device further comprises at least one camera.

20. The computer-implemented method of claim 13, wherein the defined position further comprises a defined distance from the eye of the user.

* * * * *